United States Patent [19]

Vincent et al.

[11] Patent Number: 5,191,600
[45] Date of Patent: Mar. 2, 1993

[54] X-RAY COMPUTER TOMOGRAPHY SYSTEM WITH SPLIT DETECTOR RING

[75] Inventors: Paul Vincent, Karlsruhe; Günther Laukien, Rheinstetten; Arne Kasten, Karlsruhe, all of Fed. Rep. of Germany

[73] Assignee: Bruker Analytic, Fed. Rep. of Germany

[21] Appl. No.: 695,597

[22] Filed: May 3, 1991

[30] Foreign Application Priority Data

May 11, 1990 [DE] Fed. Rep. of Germany ....... 4015180

[51] Int. Cl.$^5$ .............................................. A61B 6/03
[52] U.S. Cl. ...................................... 378/10; 378/11; 378/19
[58] Field of Search ................. 378/4, 9-16, 378/19, 62, 121, 124, 134, 136, 137, 138

[56] References Cited

U.S. PATENT DOCUMENTS

| | | | |
|---|---|---|---|
| 4,153,842 | 5/1979 | Rohmfeld | 378/19 |
| 4,158,142 | 6/1979 | Haimson . | |
| 4,239,972 | 12/1980 | Wagner | 378/9 |
| 4,352,021 | 9/1982 | Boyd et al. . | |
| 4,754,468 | 6/1988 | Mori | 378/4 |
| 4,866,745 | 9/1989 | Akai | 378/9 |

FOREIGN PATENT DOCUMENTS 83904786 3/1984 Fed. Rep. of Germany .
2034149 5/1980 United Kingdom .

OTHER PUBLICATIONS

App. Optics vol. 24, No. 23 P4052 (Peschmann et al.), "High-Speed Computed Tomography: Systems and Performance", Dec. 1985.

Primary Examiner—David P. Porta
Attorney, Agent, or Firm—Wolf, Greenfield & Sacks

[57] ABSTRACT

An X-ray computer tomography system with a ring anode and substantially without mechanically moving parts for the production of fast image slices from the inside of an object is improved in such a way that a detector ring is comprised of two adjacent parallel partial detector rings of substantially equal size, whereby the detector ring is arranged within and coplanar to the anode ring. The two partial rings of the detector ring are displaced in a direction largely pependicular to the scan slice so that a ring-shaped detector ring gap is formed between them through which the fan beam coming from the focal spot on the anode passes.

29 Claims, 6 Drawing Sheets

X-RAY COMPUTER TOMOGRAPHY SYSTEM WITH SPLIT DETECTOR RING

FIELD OF THE INVENTION

The invention concerns a detector configuration for an X-ray computer tomography system wherein neither the X-ray source nor the detectors are caused to move during the course of a scan as well as a method for the operation of such a system. X-ray computer tomographs without mechanical motion of the X-ray source or the detectors are known in the art from the U.S. Pat. Nos. 4,352,021 and 4,158,142 and the German patent publication DE 28 21 870 A1.

DESCRIPTION OF THE PRIOR ART

In conventional computer tomographs, the detector and/or the x-ray source are mechanically moved about an object being scanned during the course of the scan. In this way, it is possible for the the x-ray source and its associated x-ray fan beam and the detector to be largely coplanar. This coplanarity allows for uniform imaging slices and good image quality through the reduction of partial volume artifacts. However, due to the use of mechanical rotation, these tomographs are usually limited to scan times of about 1 second for a full 360 degree scan. In the event that no mechanical motion is necessary, significantly shorter scan times are possible, that is to say, faster scans which, for their part, can be utilized for examining quickly moving objects such as the human heart.

In U.S. Pat. Nos. 4,352,021 and 4,158,142, the moving X-ray source is replaced by an electron beam, said beam colliding with an arc-shaped anode from a direction which is largely perpendicular to the scan-slice. A method is described in U.S. Pat. No. 4,352,021 with which two dipole magnets guide the beam in such a way that its focus on the anode surface approximately describes an arc of 210 degrees. The X-rays emitted from the anode are detected by means of an arc-shaped detector configuration, whereby the detector configuration consists of two directly adjacent detector ring segments. The detector configuration lies across from the anode and likewise describes an arc of approximately 210 degrees. Therefore, neither the anode nor the detector configuration form a full circle and there is only a relatively small overlap region. The described preferred embodiment utilizes four, instead of only one, anode rings (in the following "ring" also signifies ring segment) which are each slightly displaced with respect to each other in a direction which is largely perpendicular to their respective scan planes. By guiding the electron beam successively around each of the four anodes and, for each anode scan, by measuring the X-ray intensity passing through the object in each of the adjacent detector arcs, one obtains data sets which are sufficient for the reconstruction of a total of 8 largely adjacent image slices from the object.

In U.S. Pat. No. 4,158,142 the relative geometric configuration of electron and X-ray sources is similar to that in U.S. Pat. No. 4,352,021. There are, however, differences in the electromagnetic guidance and focusing of the electron beam and there is one single complete 360 degree anode ring and one single complete 360 degree detector ring. Detector and anode rings are coaxial but not coplanar.

The possibilities for effecting faster scans in the detector configurations which are discussed in U.S. Pat. Nos. 4,352,021 and 4,158,142 are associated with reduced image quality and increased expense compared to conventional tomographs.

The fact that the anode and detector arcs are not coplanar leads to a larger and more uneven effective slice thickness and irradiation of the detectors and, thereby, to an increase in partial volume artifacts. In order to minimize these problems, the separation between the anode and the detector must be as large as possible. Such increased size involves increased cost associated both with the production of the scanner as well as with its placement and operation in, for example, a hospital environment. Moreover, the large separation between the x-ray source and detector leads, for a given electron beam intensity, to a strong reduction in the X-ray intensity reaching the detector which, in turn, results in a reduced signal to noise ratio and worse low contrast resolution. The utilization of a partial scan of only 210 degrees as described in U.S. Pat. No. 4,352,021 causes an additional reduction in the image quality compared to conventional mechanical rotating systems.

DE 28 21 870 A1 discloses an x-ray computer tomography scanner exhibiting a radiation source ring with a plurality of equally spaced radiation sources. A scan is executed by individually switching the radiation sources on and off in rotational sequence about the radiation source ring. The detector configuration consists of a plurality of individual shielded detector elements arranged in a detector ring which is concentric to the radiation source ring and of smaller diameter. Each shielded detector element is connected to a light guide. In the embodiments, each single detector element is subdivided into two or more individual detector element segments and these segments are connected to each other with one or more light guides, such that all segments in an individual detector element are read out by a common readout element such as a photomultiplier.

In a preferred embodiment of DE 28 21 870 A1, the light guide is sandwiched between two detector element segments of equal length and the length of the light guide is equal to twice that of an individual detector element segment of a shielded detector element. The detector ring and the radiation source ring are arranged largely coplanar to each other so that the fraction of the x-ray radiation to be used for imaging first passes through the light guides of the detector elements, then the object being scanned, and finally is detected by the detector elements on the opposite side of the detector ring.

The detector ring configuration according to DE 28 21 870 A1 is associated with reduced image quality and increased unused patient radiation dose compared to conventional scanners.

The use of the long light guide in the scan plane means that a large fraction of the x-ray dose incident on the patient never strikes the active portions of the detector elements and, consequently, is not actually used to construct the image. As a result, the patient's risk for developing, by way of example, cancer due to his absorbed radiation dose is increased. In addition, the unused patient dose produces scattering in the patient and a fraction of the scattered x-rays will enter the detector elements and cause background which, in turn, reduces the signal to noise ratio in the detector elements and leads to a deterioration in the low contrast resolution. There are additional reconstruction errors since, through the introduction of a light guide, the effective image slice thickness is increase which, in turn, leads to increased partial volume artifacts. In addition, there is a reduced signal to noise ratio and, thereby, reduced image quality associated not only with the fact that, through the introduction of the light guide, a "dead space" is introduced and only a fraction of the fan beam is actually measured so that, for a given x-ray source strength emerging from the focal spot, the absolute magnitude of the detected signal is reduced, but also in consequence of scattered radiation from the light guide itself, a large fraction of which enters the detector segments and produces background.

Due to the above mentioned deficiencies in high-speed X-ray computer tomographs, it is the purpose of the present invention to improve an x-ray computer tomography system for the production of image slices through an object, wherein an X-ray source is utilized consisting of an electron source and a stationary anode ring, with means for accelerating the electrons emitted from the electron source, using a high positive constant voltage, onto the anode ring, such that the electrons form an electron beam which collides at a focal spot with the anode ring which, in turn, emits X-ray radiation, and with a complete or partial X-ray detector ring with a smaller radius than the anode ring, in which the detector ring and the anode ring are coaxially arranged and define a scan slice, in such a way that the achieveable image quality, the scanner size, and the used fraction of patient dose are comparable to that of conventional scanners.

BRIEF SUMMARY OF THE INVENTION

This purpose is achieved in that the detector ring is comprised of two adjacent parallel detector partial rings of substantially equal size and the detector ring is arranged within and coplanar to the anode ring thereby defining a scan slice, wherein both partial rings of the detector ring are displaced in a direction which is largely perpendicular to the scan slice so that a ring-shaped detector ring gap is formed between them through which the fan beam emanating from the focal spot on the anode passes.

In this manner, the underlying purpose of the invention is fully achieved. The utilization of two partial detector rings with a ring gap between them allows for the coplanar arrangement of the anode and detector rings as well as for the extension of both the anode and detector rings through more than 180 degrees, for example, a full 360°, thereby allowing full 360° scans. The fan beam emanating from a focal spot on the anode must, namely, no longer pass by the side of the detector ring, and instead can pass through this ring at the detector ring gap. As a result, the system can be compact without leading to coplanarity problems. The absence of the long light guide reduces unused patient dose and results in improved signal to noise ratios as well as thinner slices and reduced partial volume artifacts. The ability to read out the two adjacent image slices separately leads to still thinner slice capability and higher resolution.

In a preferred embodiment of the invention, the detector ring is located inside of the electron source ring said ring being comprised of, rather than one single electron source positioned far from the anode ring, a plurality of individual electron sources which, for their part, are attached rigidly to a stationary ring located in proximity to the ring anode. This electron source configuration is the object of a parallel patent application filed on the same date entitled "X-Ray Computer Tomography System" by inventors P. Vincent, G. Laukien, and A. Kasten and corresponding to German patent application P 40 15 105.0-33, and the contents disclosed in this application are, through this reference, caused to become part of the contents disclosed in the present application.

In a preferred embodiment there are approximately 250 of such electron sources at constant angular intervals on a circular ring the radius of which is approximately 400 mm, and the electron sources are approximately at ground potential and the anode between approximately +100 kV to +150 kV, preferentially, approximately +130 kV. The electron sources and the anode ring are located in a common vacuum housing and the electron sources are individually controllable to emit electron beams in a predetermined time sequence. The electrons emanating from the electron source are focussed into a beam which collides with the anode at a focal spot and produces X-ray radiation (substantially Bremsstrahlung) from which a fan-shaped X-ray beam (fan beam) is collimated.

In a preferred embodiment, the X-ray radiation coming from the focal spot which has passed through the object is detected in a complete 360 degree X-ray detector ring, with the detector ring being composed of two adjacent parallel partial rings of equal radius. The partial rings are displaced in a direction which is largely perpendicular to the scan slice so that a ring-shaped gap is formed between them, and the detector ring and the anode ring are coaxial and coplanar to each other so that the two rings define a largely planar scan region wherein the fan beam is located. The gap between the two detector partial rings is large enough for the entire fan beam with the desired slice thickness to pass through, but small enough that most of the radiation passing through the object can also be detected, that is to say, hits the detector ring. Therefore, in a particularly advantageous fashion, the detector ring gap is so dimensioned that the detector elements on the opposite side are just barely illuminated.

In a particularly preferred embodiment, the detector ring has a radius of approximately 330 mm and each partial ring contains 1200 individual detector elements which are suited for the detection of X-ray radiation coming from the focal spot on the anode ring. Other embodiments with elliptical instead of circularly shaped detector and anode rings are possible.

The slice thickness of the scan is adjustable through a relative displacement of the two detector partial rings in a direction which is largely perpendicular to the scan slice, such that each detector ring is displaced equally but in opposite directions in order to change the width of the detector ring gap. The geometry of the system is so arranged that the relationship $R_d/R_f=(w_d-g)/(w_d+g)$ is approximately observed, whereby g is the width of the gap between the detector partial rings, $w_d$ the width of the fan beam after passing through the object at the detector ring location across from the focal spot, $R_d$ the detector ring radius, and $R_f$ the radius of the focal spot. In a particularly advantageous embodiment of the invention $R_d=330$ mm, $R_f=400$ mm, and $g/w_d=0,1$.

In one embodiment, each electron source consists of a heated filament for the production of the electrons and a hollow cathode. In a thereby particularly preferred embodiment, the hollow cathode is subdivided in two or more segments which are electrically isolated with respect to each other. By applying, relative to the filaments, negative voltages up to several kV which are of adjustable strength on one or more of the hollow cathode segments, it is possible to switch on and switch off, focus and steer the electron beam emanating from the cathode. The shape of the hollow cathode and its distance from the anode are so chosen that the electrons emanating from each of the filaments are focussed into a beam which, in turn, is accelerated into a collision at the focal spot on the anode. Methods for calculation of electron paths for given potential distributions taking into consideration space charge effects are known to one of average skill in the art. By sequentially pulsing (in general, controlling) the voltages on the hollow cathode segments, it is possible to produce a ring source of X-ray radiation, such that any and each segment of the ring can be caused to emit X-ray radiation in a given time sequence.

In a preferred embodiment, the detector elements of both partial rings are rotated with respect to each other by an angle which corresponds approximately to half the angular width of an individual detector element. During the course of a scan, the data from each individual one of the, altogether, 2400 detector elements is registered and processed. Additional detectors are arranged outside of the scan slice in the environment of the detector rings in order to track scatter contributions and changes in the X-ray source intensity.

The small radius of the preferred embodiment of the invention leads to a strong increase in the X-ray intensity for a given slice thickness, scan time and reconstruction or field of view compared with those which are typically achieved, for example, in the U.S. Pat. Nos. 4,352,021 and 4,158,142 which, in turn, leads to a better signal to noise ratio in the detectors and to better low contrast resolution. In addition, for a given total number of individual detector elements, the small radius of the detector ring leads to a reduction in the individual detector element sizes and, thereby, to improved spatial resolution. The proximity of the individual electron sources to the anode reduces the problems associated with the expansion of the electron beam at large beam intensities as a result of space charge effects which, in turn, facilitates smaller focal spots and, thereby, a further improvement in the spatial resolution and the frequency bandpass of the system.

It is possible, for the data from the, preferentially, approximately 2400 detector elements of both detector rings to be read out and processed in such a way that two adjacent image slices are reconstructed, with the data of one detector partial ring being evaluated for each slice (two slice analysis).

Alternatively the data from all of the 2400 detectors can be utilized in order to reconstruct a common image slice of double the slice thickness with, however, improved spatial resolution in the slice (one slice analysis).

In the one slice analysis, the advantageous fact that, one detector partial ring is rotated with respect to the other by approximately half of the detector element width (more exactly: by half the arc length corresponding to the circumference of the detector ring divided by the number of detectors in one partial ring) results in a doubling of either the number of view angles per scan or the number of data points per view angle compared to the two slice analysis and, thereby, in a better spatial resolution within the slice (however, with approximately double the slice thickness).

Further advantages can be derived from the description and from the accompanying drawings. Clearly, the characterizing features mentioned above as well as those to be explained below can be applied not only in the corresponding combination given but also in other combinations or by themselves without departing from the framework of the current invention.

Embodiments of the invention are given in the drawings and are explained in the following description. Shown are.

BRIEF DESCRIPTION OF THE DRAWING

DETAILED DESCRIPTION OF THE PREFERRED EMBODIMENTS

Figure 1:
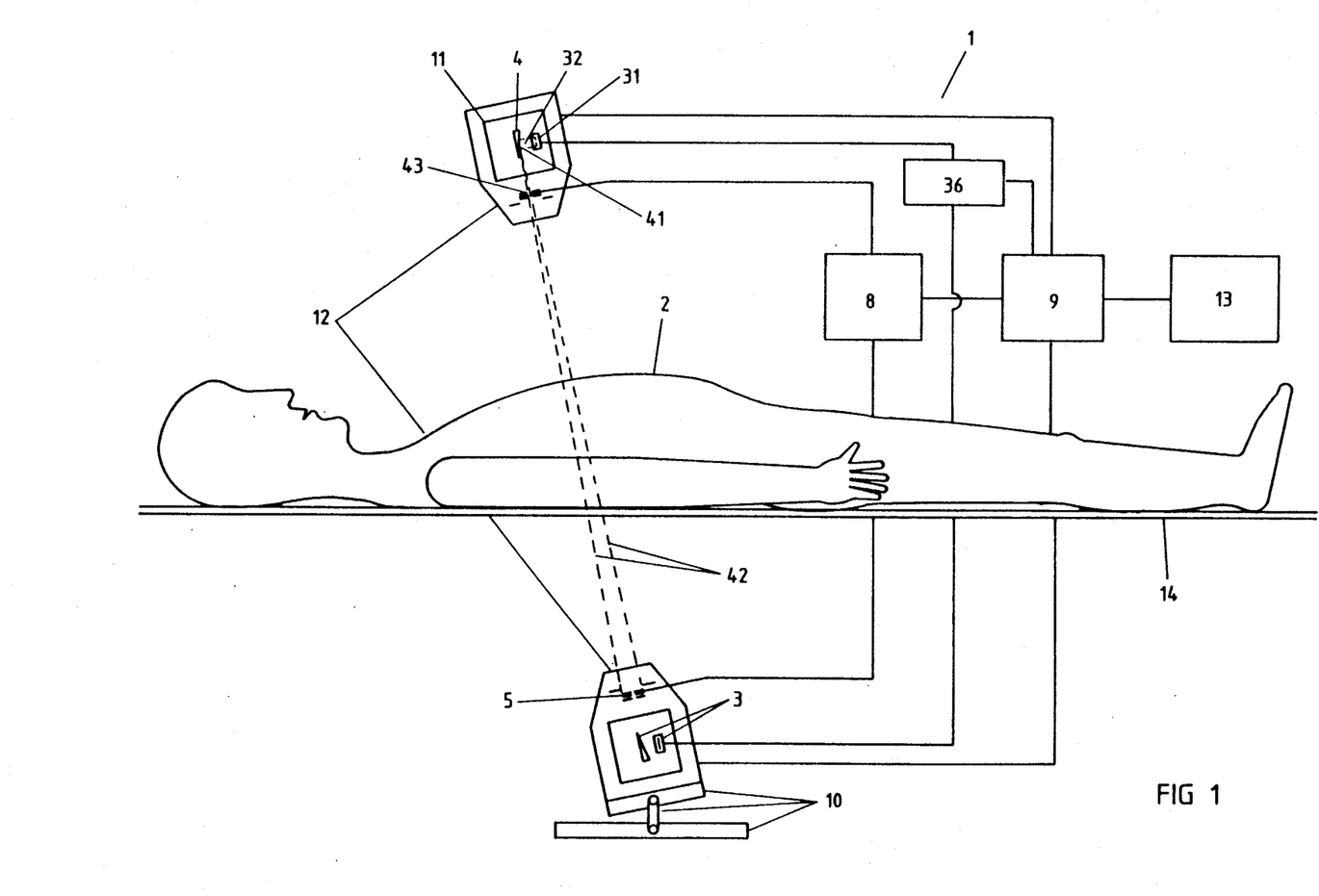
FIG. 1: A schematic representation of an embodiment of an X-ray computer tomography system according to the invention.

FIG. 1 shows an overall view of an embodiment of an X-ray computer tomography system (1) according to the invention. An X-ray source (3) which is comprised of a plurality of electron sources (31) and anode ring (4), both of which are located within a common vacuum housing (11), produces X-ray radiation at the position of a focal spot (41) said radiation coming from collisions between electrons from an electron beam (32) of the electron source (31) with the anode ring (4). The X-ray radiation coming from the position of the focal spot (41) is collimated into a fan beam (42) with a beam collimator (43) before passing through the object (2) being studied, with this object being located within the opening of the gantry (12) at a desired position through translation of a moveable support structure (14). After the fan beam (42) has passed through the object (2), it is detected in a detector ring (5). The X-ray intensity passing through the object (2) is converted into electrical signals by the detector elements in the detector ring (5) the magnitudes of which are largely linearly proportional to the X-ray intensity incident upon the corresponding detector element. The signals are then digitized in analog digital converters (8) and passed onto a computer (9). The computer controls and monitors the scan functions and can either be configured as an individual computing unit or as a network of coupled or uncoupled computing units. The scan functions named include, among others, means (36) for controlling the electron sources (31). The computer reconstructs an image slice through the object using data taken with the detector elements of the detector ring (5). These image slices are, by way of example, displayed on a display screen (13). A tilt mechanism (10) is provided for in order to tilt the gantry (12) from the vertical over a given angular region.

Figure 2A:
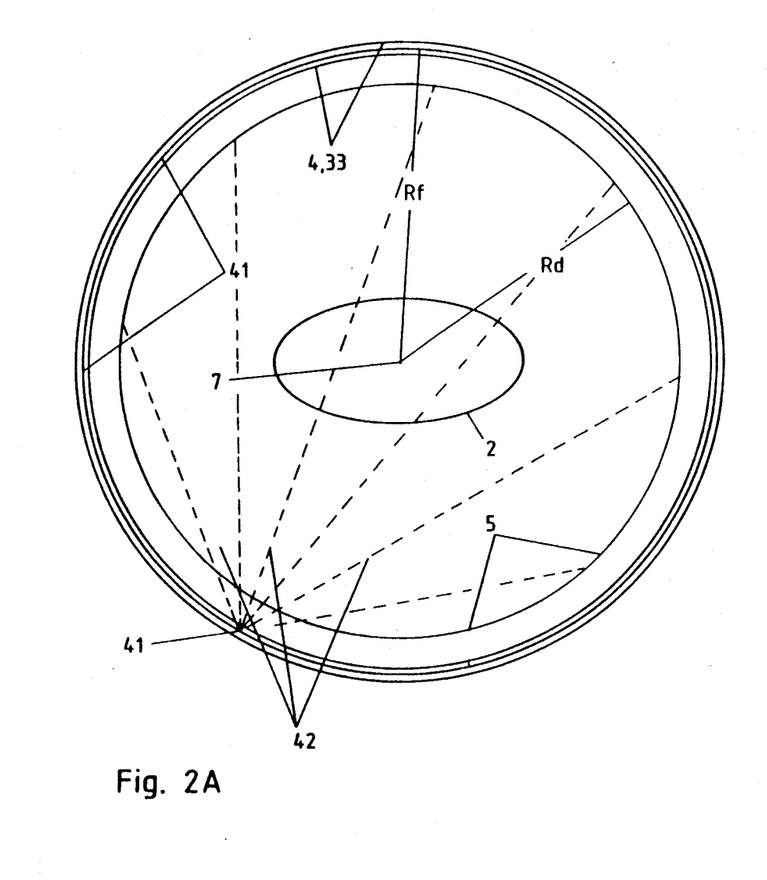
FIG. 2A: A front view of the system geometry.
Figure 2B:
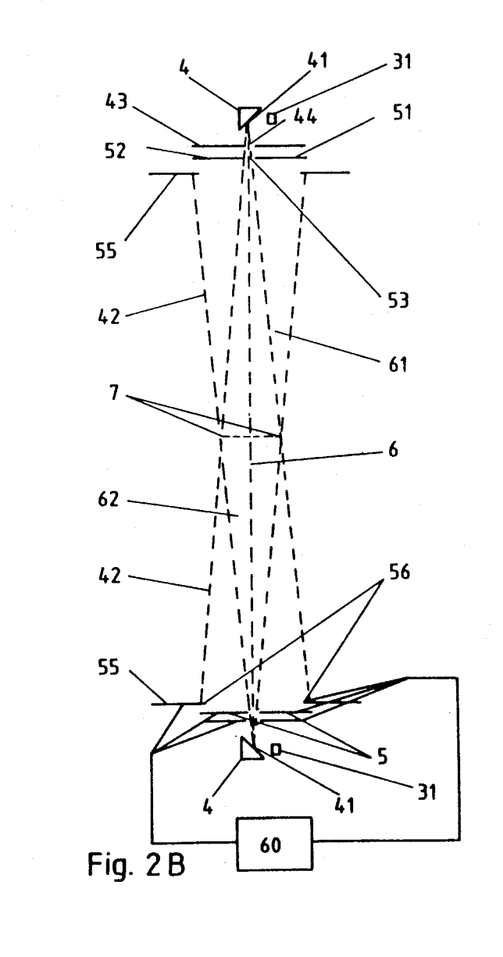
FIG. 2B: A side view of the system geometry.

FIG. 2A and FIG. 2B show the fundamental geometry of a preferred version of the invention. FIG. 2A shows a front view and FIG. 2B a cross section or side view. The possible positions of the focal spot (41) on the anode ring (4) describe a circle of radius $R_f$ which is concentric with the detector ring (5) of radius $R_d$, whereby $R_f$ is larger than $R_d$. A plurality of electron sources (31) are arranged on an electron source ring (33) which is located in proximity of the anode ring (4). The fan beam (42) originates from one of the several corresponding locations of the focal spot (41) on the anode ring (4). An object (2) is located near the center (7) of the anode and detector ring. X-ray radiation emanating from the focal spot (41) is collimated into a fan beam (42) with a beam collimator (43) which is located between the anode (4) and detector rings (5) in that said radiation passes through the beam collimator gap (44). The fan beam (42) passes through the detector ring gap (53), the object (2), and is further collimated by the detector collimator gap (56) of the detector collimator (55) before being detected in the detector elements of the detector ring (5). As the focal spot (41) moves about the anode ring (4), the fan beam (42) cuts through the object (2) in an approximately planar slice (6), said slice consisting of two neighbouring partial slices (61, 62), whereby a partial slice (61) is comprised largely from the portion of the fan beam incident upon one detector partial ring (51), and the other partial slice (62) from the portion which illuminates the other partial detector ring (52). Means (60) are available for varying the thickness of the planar slice (6) or partial slices (61,62) respectively, by adjusting the width of the beam collimator gap (44), the detector ring gap (53), and the detector collimator gap (56).

Figure 3:
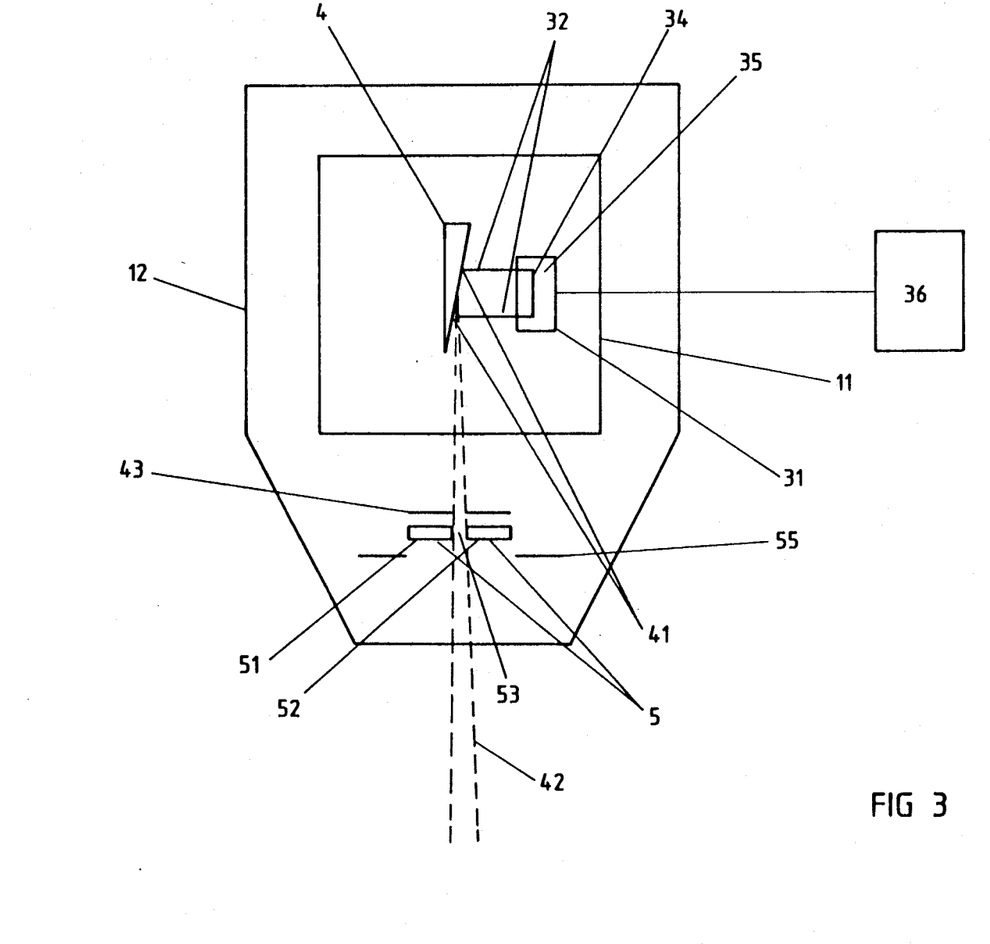
FIG. 3: An enlarged cross section through the gantry with the devices for the production and detection of the fan beam.

FIG. 3 shows a cross section through one portion of the gantry (12). Means (36) are provided for controlling the electron sources (31), with these means (36) being capable of applying time and position varying voltages on the surface of the hollow cathodes (35). By varying these voltages, it is possible to switch on and off as well as focus and steer the electron beam (32) coming from the filament (34). The electron beam (32) collides with the anode ring (4) at the focal spot (41) location and effects the emission of X-ray radiation. The electron sources (31) and anode ring (4) are located in a common vacuum housing (11). The X-ray radiation emitted from the focal spot (41) is collimated into a fan beam (42) with a beam collimator (43), such that the fan beam passes through the detector ring gap (53) which separates both partial detector rings (51, 52) of the detector ring (5). The detector collimator (55) limits the effective width of the fan beam (42) emanating from the focal spot at the opposite side of the anode ring (4) after it has passed through the object.

Figure 4:
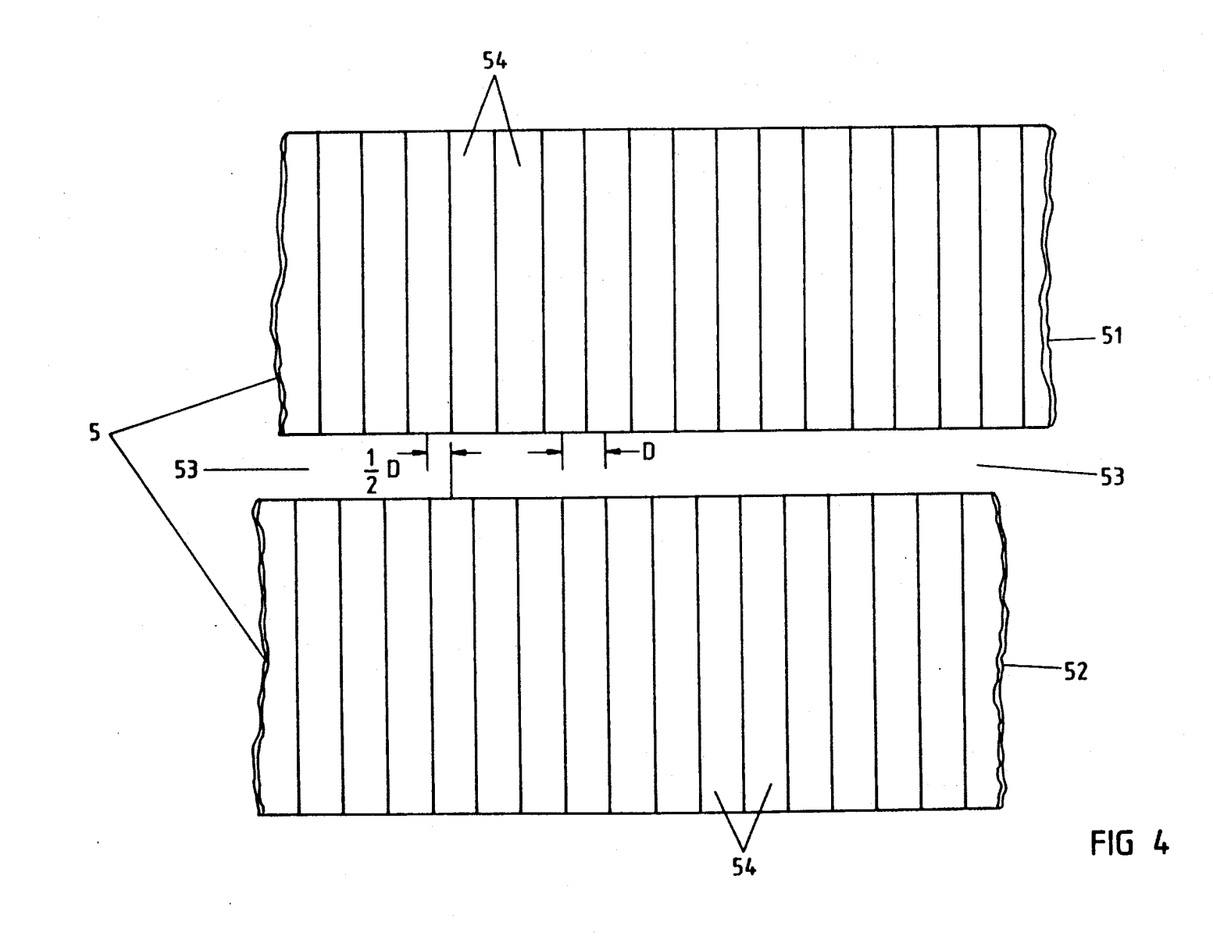
FIG. 4: The detector ring viewed from the center of the anode and detector rings.

FIG. 4 gives a view of a portion of the detector ring (5) as seen from the center of the anode (4) or detector ring (5). The detector ring (5) consists of two detector partial rings (51, 52) which are separated by a detector ring gap (53). Each detector partial ring (51, 52) includes a plurality of individual detectors or detector elements (54). In a preferred embodiment of the invention there are 1200 such detector elements (54) in each of the two detector partial rings (51, 52) for a total of 2400 detector elements (54). The signal from each detector element (54) is digitalized in an analog digital converter and the data so obtained utilized by a computer to generate an image slice through the object. It is particularly preferred when the two detector partial rings (51, 52) are rotated with respect to each other by an arc length D/2 which corresponds to the detector ring circumference divided by twice the number of detector elements (54) per detector partial ring (51 or 52).

Figure 5:
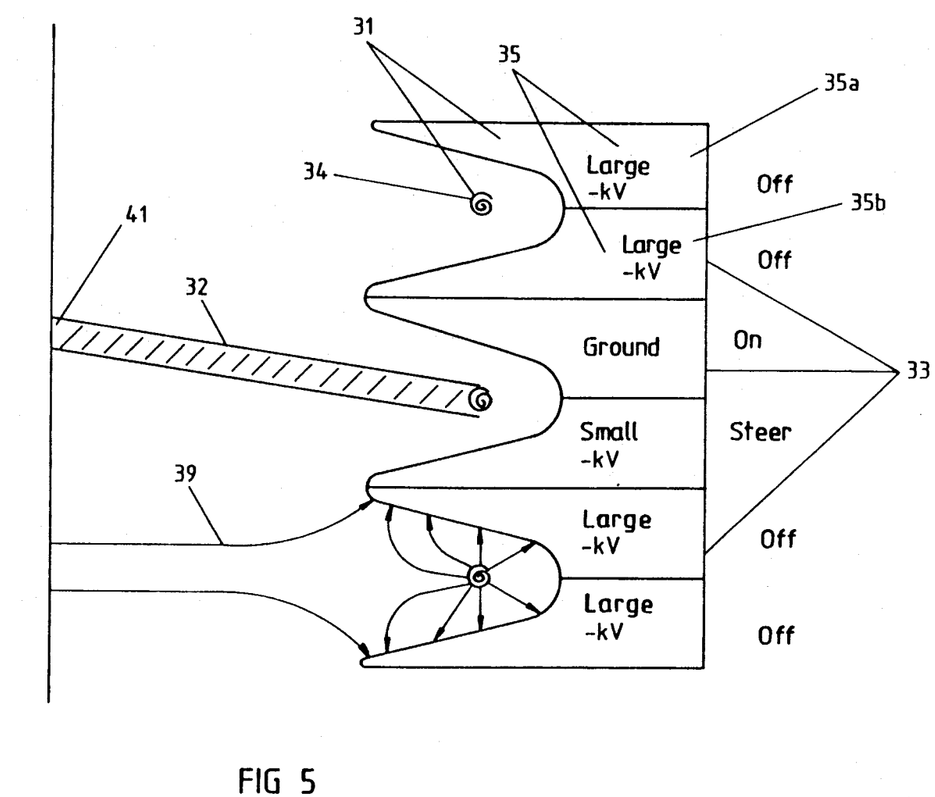
FIG. 5: A qualitative representation of the principle of production of the fan beam.

FIG. 5 qualitatively describes the principle of operation of a preferred version for the production of the electron beam (32). FIG. 5 shows a section of the anode (4) and electron source ring (33) as viewed from the center of the anode (4) or detector ring (5) respectively. The electron source ring (33) consists of an array of adjacent electron sources (31) which are located in close proximity to the anode ring (4). FIG. 5 explicitly shows three electron sources (31).

In a preferred embodiment of the invention, each electron source (31) consists of a hollow cathode (35) and a heatable filament (34). The hollow cathode (35) is subdivided into two segments which are electrically isolated from each other. The anode ring (4) is at an electrical potential of +130 kV relative to the filament (34), and the filament (34) is preferentially at ground potential. The shape of the hollow cathodes (35) and their distance from the anode ring (4) are so chosen that the electrons emitted from the corresponding filaments (34) are focussed into an electron beam (32) and accelerated to a focal spot (41) on the anode ring (4). Through the application of appropriate negative voltages of up to several kV (relative to the filaments) of various strength on one or more of the hollow cathode segments (35a, b) of an electron source (31), it is possible to switch on and off or focus and steer the corresponding electron beams (32). The position of the focal spot (41) of the electron beam (32) of a given electron source (31) on the anode ring (4) is determined by the voltages which are applied to the two segments (35a, b) of the hollow cathode (35) of the electron source (31). The electrical field lines (39) corresponding to the voltage state wherein the electron source (31) is switched off, that is to say, there are essentially no electrons emanating from the filament (34), are qualitatively represented in one electron source (31) in FIG. 5. During the time duration of a scan, the voltages on the anode ring (4) are held constant and the potentials of the hollow cathode segments (35a, b) are varied. Means (49) are provided for supporting the anode ring and for isolating it with respect to ground potential, as well as means (48) for providing high voltage to it (preferentially +130 kV). Varying associated embodiments are possible with which the voltage level of the anode ring (4), the hollow cathodes (35), and the filaments (34) are shifted with respect to ground potential by a predetermined voltage amount.

Figure 6A:
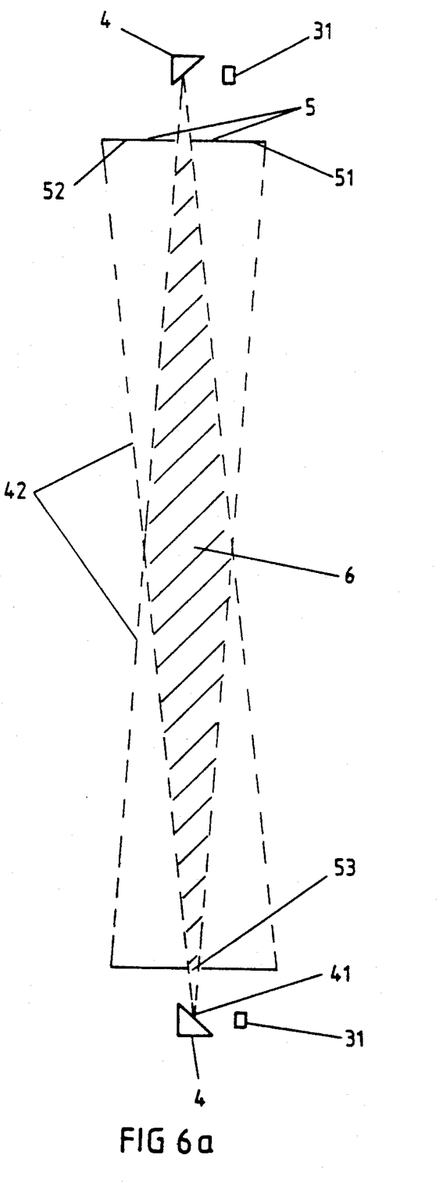
FIG. 6A: A comparison of the relative configuration of the X-ray source, fan beam and detector rings in cross sectional view according to the invention.
Figure 6B:
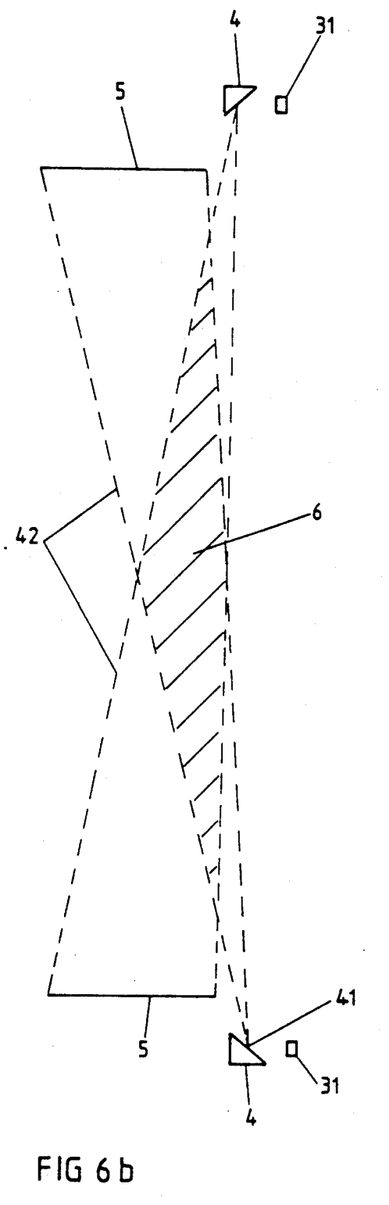
FIG. 6B: A comparison of the relative configuration of the X-ray source, fan beam and detector rings in cross sectional view according to prior art.

FIG. 6A compares a schematic section through the scan region of an X-ray tomography system according to the invention with prior art (illustrated in FIG. 6B). In prior art (FIG. 6B), the anode (4) and the detector rings (5) are arranged coaxially but not coplanar so that, during a scan, the overlap region (cross hatched) of all fan beams (42) defines a scan slice (6) whose form, due to the non-coplanarity of the anode (4) and detector rings (5), deviates substantially from a slice of constant thickness, which, for its part, leads to partial volume artifacts. According to the invention (FIG. 6A), the splitting of the detector ring (5) into two detector partial rings (51, 52) with a detector ring gap (53) allows for a substantially coplanar configuration of the detector (5) and anode ring (4), so that a scan slice (6) with more uniform thickness is achieved.

We claim:

1. In an X-ray computer tomography system for generating an image, having a desired slice thickness, of an object, the system having an electron source for generating electrons and a stationary anode, means for applying an electric potential between the electron source and the anode to accelerate the electrons from the electron source to the anode so that the electrons collide with the anode at a focal spot and generate X-ray radiation which passes through the object, a detector responsive to the X-ray radiation for generating image signals, and means responsive to the image signals for generating the image, the improvement being that the detector is comprised of two partial detector rings mutually displaced from one another so that a gap having a width is formed between them and the tomography system comprises means for mounting the partial detector rings on either side of the focal spot so that X-ray radiation emanating from the focal spot passes through the gap, and means responsive to the desired slice thickness for moving the partial detector rings towards and away from each other in order to adjust the gap width so that substantially all of the x-ray radiation corresponding to the desired slice thickness passes through the gap and most of the radiation passing through the object is detected.

2. In an X-ray computer tomography system, the improvement according to claim 1 wherein the anode comprises an anode ring and the two partial detector rings exhibit the following features:
   they are substantially equal to each other in size,
   they are arranged coaxial to and within the region encompassed by the anode ring, and
   they are comprised of a plurality of separate detector devices which provide position sensitive X-ray detection.

3. In an X-ray computer tomography system, the improvement according to claim 2 wherein the two partial detector rings and the anode ring are arranged in a substantially coplanar fashion to define a scan slice.

4. In an X-ray computer tomography system, the improvement according to claim 2 wherein both the anode ring and the detector are substantially circularly shaped.

5. An X-ray computer tomography system for generating an image, having a desired slice thickness, of an object comprising:
   a stationary ring-shaped anode having a center;
   a stationary electron source means;
   means for controlling the electron source means to generate electrons in a predetermined time sequence;
   means for applying an electric potential between the electron source means and the anode to accelerate the electrons from the electron source means to the anode so that the electrons collide with the anode at a focal spot to generate X-ray radiation;
   a beam collimator for collimating the X-ray radiation from the focal spot into a fan beam, the fan beam passing through the object;
   a detector responsive to X-ray fan beam radiation which has passed through the object for generating image signals, said detector comprising two partial detector rings which are mutually displaced with respect to each other so that a ring-shaped gap having a width is formed between them, each of the partial detector rings being comprised of a plurality of discrete detector devices providing position sensitive X-ray detection;
   means for mounting each of the partial detector rings coaxial, and substantially coplanar, to, and within, the region encompassed by the anode ring and on either side of the focal spot so that X-ray radiation emanating from the focal spot passes through the gap; and
   means responsive to the desired slice thickness for moving the partial detector rings towards and away from each other in order to adjust the gap width so that substantially all of the x-ray radiation corresponding to the desired slice thickness passes through the gap and most of the radiation passing through the object is detected.

6. An X-ray computer tomography system according to claim 5 wherein the electron source means comprises a plurality of substantially equally spaced electron sources are arranged in a coaxial electron source ring, the electron source ring being located in proximity to the anode ring.

7. An X-ray computer tomography system according to claim 5 wherein each of the partial detector rings and the anode ring are substantially circularly shaped.

8. An X-ray computer tomography system according to claim 5 wherein each of the partial detector rings spans an arc of 360 degrees.

9. An X-ray computer tomography system according to claim 5 wherein the geometrical relationship:

$$R_d/R_f = (wd-g)/(wd+g)$$

is approximately satisfied, in which g is the width of the gap between the partial detector rings, wd the width of the X-ray radiation fan beam at the position at which the X-ray radiation fan beam impinges on the partial detector rings, Rd is the radius of each of the partial detector rings and Rf is the distance from the focal spot to the anode ring center.

10. An X-ray computer tomography system for the production of image slices having a desired thickness through an object, the system comprising:
   a plurality of stationary electron sources arranged in a planar ring, each of said plurality of electron sources comprising a filament for the generation of electrons, a cathode partially surrounding the filament, and means for applying voltages to the partially surrounding cathode;
   a stationary ring-shaped planar anode positioned coaxially with and in proximity to the electron source ring;
   means for accelerating electrons emitted from each of the plurality of electron sources towards the anode ring, whereby the electrons from each of the plurality of electron sources form an electron beam which collides with the anode ring at a focal spot to produce X-ray radiation;
   means for collimating the X-ray radiation emanating from the focal spot into an X-ray fan beam which passes through the object;
   a detector ring responsive to the X-ray fan beam radiation for generating image signals, said detector ring comprising two partial detector rings each being substantially equal in size and mutually displaced with respect to another so that a ring-shaped gap having a width is formed between them;
   means for mounting the partial detector rings on either side of the focal spot so that X-ray radiation emanating from the focal spot passes through the gap, and each of the partial detector rings is coaxial with, substantially parallel to, and substantially coplanar with the anode ring and is arranged within the region encompassed by the anode ring;

means responsive to the desired image slice thickness for moving the partial detector rings towards and away from each other in order to adjust the gap width so that substantially all of the x-ray radiation corresponding to the desired image slice thickness passes through the gap and most of the radiation passing through the object is detected; and means for controlling each of the plurality of electron sources so that the plurality of electron sources emit electron beams in a predetermined time sequence and so that the focal spots produced by the electron beams on the anode ring are each electron magnetically swept over a predetermined portion of the anode ring wherein the controlling means controls the voltage applying means in each of the plurality of electron sources to apply a temporally and spatially variable voltage to the partially surrounding cathode in order to sweep the electron beam generated by each electron source.

11. An X-ray computer tomography system according to claim 10 wherein the geometrical relationship:

$$R_d/R_f = (wd-g)/(wd+g)$$

is approximately satisfied, in which g is the width of the detector ring gap, wd the width of the X-ray radiation fan beam at the position of the detector ring opposite to an electron beam focal spot which generated the X-ray radiation, Rd is the distance from the detector ring to the detector ring center and Rf is the distance from the focal spot to the anode ring center.

12. An X-ray computer tomography system according to claim 10, further comprising a pair of ring-shaped beam collimators located coaxially with the electron source ring and positioned on either side of the anode ring to form a beam collimator gap between the beam collimators and means for adjusting the separation of the detector partial rings and the separation of the beam collimators to change the thickness of a scan slice through the object.

13. An X-ray computer tomography system according to claim 10, wherein each of the detector partial rings is comprised of a predetermined plurality of detector elements and the detector partial rings are rotated with respect to each other so that detector elements of the two partial rings are displaced with respect to each other by a distance of one-half the width of a detector element.

14. An X-ray computer tomography system according to claim 10, wherein the partially surrounding cathodes are each subdivided into a plurality of segments which, in turn, are electrically insulated with respect to each other and wherein means are provided for applying differing voltages to said partially surrounding cathode segments so that the electron beam is focussed onto and swept across the anode.

15. An X-ray computer tomography system for the production of image slices through an object, the system comprising:

a plurality of stationary electron sources arranged in a planar ring, each of said plurality of electron sources comprising a filament for the generation of the electrons, a cathode partially surrounding the filament, said cathode being subdivided into a plurality of segments are electrically isolated with respect to each other and means for applying voltages to the partially surrounding cathode;

a stationary ring-shaped planar anode positioned coaxially with and in proximity to the electron source ring;

means for accelerating electrons emitted from each of the plurality of electron sources towards the anode ring, whereby the electrons from each of the plurality of electron sources form an electron beam which collides with the anode ring at a focal spot to produce X-ray radiation;

means for collimating the X-ray radiation emanating from the focal spot into an X-ray fan beam;

a detector responsive to the X-ray radiation for generating image signals said detector comprising two partial detector rings said partial detector rings mutually displaced with respect to another so that a ring-shaped gap is formed between them through which X-ray emanating from the focal spot pass with said partial detector rings exhibiting the following features:
A. they are substantially equal to each other in size,
B. they are coaxial and substantially coplanar to the anode ring,
C. they are arranged within the region encompassed by the anode ring,
D. they are arranged substantially parallel to the anode ring, means for controlling the voltage applying means in each of the plurality of electron sources to apply a temporarily and spatially variable voltage to the partially surrounding cathode and to apply differing voltages to the partially surrounding cathode segments so that the plurality of electron sources emit electron beams in a predetermined time sequence and so that each electron beam is focussed onto and electromagnetically swept over a predetermined portion of the anode ring.

16. A method for operating an X-ray computer tomography system to form an image with a predetermined slice thickness of an object, said system having a stationary anode, a plurality of stationary electron sources in proximity to the anode each of which is controllable to generate an electron beam, means for applying an electric potential between each of the electron sources and the anode to cause the electron beam generated by each source to collide with the anode at a focal spot and to generate X-ray radiation, means for collimating the X-ray radiation emanating from a focal spot into an X-ray fan beam, means for electromagnetically sweeping each focal spot over a predetermined portion of the anode, means for detecting the X-ray fan beam comprising two partial detector rings which are mutually displaced with respect to each other so that a ring-shaped gap is formed between them through which x-ray radiation emanating from the focal spot passes, the method comprising the steps of:
A. displacing the two partial detector rings so that the ring-shaped gap formed between them has a width which allows substantially all of the x-ray radiation corresponding to the predetermined slice thickness to pass through and allows most of the radiation passing through the object to be detected;
B. controlling each of the plurality of electron sources so that none of the plurality of electron sources generates an electron beam;
C. selecting one of said plurality of electron sources;

D. controlling the selected electron source to generate an electron beam to form a focal spot;

E. controlling the sweeping means to move the focal spot formed in step C over the predetermined portion of the anode ring;

F. controlling the selected electron source to stop generation of the electron beams;

G. selecting another one of the plurality of electron sources and

H. repeating steps D through G until a predetermined number of the plurality of electron sources have been selected.

17. A method for operating an X-ray computer tomography system according to claim 16 wherein the focal spot is caused to span an arc of at least 180 degrees.

18. A method for operating an X-ray computer tomography system according to claim 16 wherein the method further comprises the steps of:

I. detecting X-ray radiation generated from the focal spot on the anode with the two partial detector rings after the X-ray radiation has passed through an object; and J. constructing two separate images of two neighboring partial slices through the object from the X-ray radiation detected in step I.

19. A method for operating an X-ray computer tomography system according to claim 16 the method further comprising the steps of:

K. detecting X-ray radiation generated from the focal spot on the anode with the two partial detector rings after the X-ray radiation has passed through an object; and L. constructing a single image of a slice through the object from the X-ray radiation detected in step K.

20. A method for operating an X-ray computer tomography system according to claim 16 wherein each of the detector partial rings is comprised of a predetermined plurality of detector elements and the detector partial rings are rotated with respect to each other so that detector elements of the two partial rings are displaced with respect to each other by a distance of one-half the width of a detector element and the method further comprises the steps of:

M. detecting X-ray radiation generated from the focal spot on the anode with the two partial detector rings after the X-ray radiation has passed through an object; and N. constructing a single image of a slice through the object from the X-ray radiation detected in step M.

21. In an X-ray computer tomography system for generating an image of an object, the system having an electron source and a stationary anode, means for applying an electric potential between the electron source and the anode to accelerate the electrons from the electron source to the anode so that the electrons collide with the anode at a focal spot and generate X-ray radiation, a detector ring responsive to the X-ray radiation for generating image signals, the detector ring being comprised of two partial detector rings mutually displaced from another so that a gap is formed between them through which X-ray radiation emanating from the focal spot passes, and means responsive to the image signals for generating an image, the improvement comprising:

means for positioning the partial detector rings relative to one another in accordance with the geometrical relationship:

$$R_d/R_f = (wd-g)/(wd+g)$$

in which g is the width of the detector ring gap, wd the width of the X-ray radiation fan beam at the position of the detector ring opposite to an electron beam focal spot which generated the X-ray radiation, $R_d$ is the distance from the detector ring to the detector ring center and $R_f$ is the distance from the focal spot to the anode ring center.

22. In an X-ray computer tomography system, the improvement according to claim 21 wherein the anode comprises an anode ring and the two partial detector rings exhibit the following features:

they are substantially equal to each other in size, they are arranged coaxial to and within the region encompassed by the anode ring, and they are comprised of a plurality of discrete detector devices to provide position sensitive x-ray detection.

23. In an X-ray computer tomography system, the improvement according to claim 21 wherein the two partial detector rings and the anode ring are arranged in a substantially coplanar fashion to define a scan slice.

24. In an X-ray computer tomography system, the improvement according to claim 21 wherein both the anode ring and the detector are substantially circular shaped.

25. A method for operating an X-ray computer tomography system having a stationary anode, a plurality of stationary electron sources located in proximity to the anode, each of the plurality of electron sources being controllable to generate an electron beam, means for applying an electric potential between each of the plurality of electron sources and the anode to cause the electron beam generated by each source to collide with the anode at a focal spot and to generate X-ray radiation, means for collimating the X-ray radiation emanating from a focal spot into an X-ray fan beam, means for electromagnetically sweeping each focal spot over a predetermined portion of the anode, detector ring means for detecting the X-ray fan beam comprising two partial detector rings which are mutually displaced with respect to each other so that a ring-shaped gap is formed between them through which x-ray radiation emanating from the focal spot passes, the method comprising the steps of:

A. assuring the geometrical relationship:

$$R_d/R_f = (wd-g)/(wd+g)$$

is approximately satisfied, in which g is the width of the detector ring gap, wd is the width of the X-ray radiation fan beam at the position of the detector ring means opposite to an electron beam focal spot which generated the X-ray radiation, $R_d$ is the distance from the detector ring means to the detector ring means center and $R_f$ is the distance from the focal spot to the anode ring center B. controlling each of the plurality of electron sources so that none of the plurality of electron sources generates an electron beam;

C. selecting one of said plurality of electron sources;

D. controlling the selected electron source to generate an electron beam to form a focal spot;

E. controlling the sweeping means to move the focal spot formed in step C over the predetermined portion of the anode ring;

F. controlling the selected electron source to stop generation of the electron beams;

G. selecting another one of the plurality of electron sources and

H. repeating steps D through G until a predetermined number of the plurality of electron sources have been selected.

26. A method for operating an X-ray computer tomography system according to claim 25 wherein the focal spot is caused to move over an arc of at least 180 degrees.

27. A method for operating an X-ray computer tomography system according to claim 25 wherein the method further comprises the steps of:

I. detecting x-ray radiation generated from the focal spot on the anode with the two partial detector rings after the x-ray radiation has passed through the object; and J. constructing two separate images of two neighboring partial slices through the object from the x-ray radiation detected in step I.

28. A method for operating an X-ray computer tomography system according to claim 25 wherein the method further comprising the steps of:

K. detecting x-ray radiation generated from the focal spot on the anode with the two partial detector rings after the x-ray radiation has passed through the object; and L. constructing a single image of a slice through the object from the x-ray radiation detected in step J.

29. A method for operating an X-ray computer tomography system according to claim 25 wherein each of the detector rings is comprised of a predetermined plurality of detector elements and the detector partial rings are rotated with respect to each other so that detector elements of the two partial rings are displaced with respect to each other by a distance of one-half the width of a detector element and the method further comprises the steps of:

L. detecting x-ray radiation generated from the focal spot on the anode with the two partial detector rings after the x-ray radiation has passed through the object; and M. constructing a single image of a slice through the object from the x-ray radiation detected in step L.

* * * * *